United States Patent [19]
Foreman et al.

[11] Patent Number: 5,703,112
[45] Date of Patent: Dec. 30, 1997

[54] METHOD OF PREVENTING EMESIS USING TETRAHYDROBENZ [CD]INDOLE-6-CARBONXAMIDES

[75] Inventors: Mark M. Foreman; J. David Leander, both of Indianapolis, Ind.

[73] Assignee: Eli Lilly and Company, Indianapolis, Ind.

[21] Appl. No.: 560,174

[22] Filed: Nov. 17, 1995

Related U.S. Application Data

[63] Continuation of Ser. No. 75,198, Jun. 10, 1993, abandoned.
[51] Int. Cl.$^6$ .................. A61K 31/40; C07D 209/90
[52] U.S. Cl. ............................ 514/411; 548/436
[58] Field of Search .......................... 514/411; 548/436

[56] References Cited

U.S. PATENT DOCUMENTS

| | | | |
|---|---|---|---|
| 4,110,339 | 8/1978 | Bach et al. | 260/326.9 |
| 4,521,421 | 6/1985 | Foreman | 514/267 |
| 4,576,959 | 3/1986 | Flaugh | 514/411 |
| 4,745,126 | 5/1988 | Leander | 514/411 |
| 4,943,428 | 7/1990 | Lucot et al. | 424/10 |
| 5,021,438 | 6/1991 | Junge et al. | 514/373 |
| 5,096,908 | 3/1992 | Gidda et al. | |
| 5,204,340 | 4/1993 | Flaugh et al. | 514/411 |
| 5,258,379 | 11/1993 | Gidda et al. | |
| 5,302,612 | 4/1994 | Flaugh et al. | 514/411 |

FOREIGN PATENT DOCUMENTS

| | | |
|---|---|---|
| 566758 | 7/1985 | Australia. |
| 0 162 695 | 11/1985 | European Pat. Off.. |
| 0 392 768 | 10/1990 | European Pat. Off.. |
| 444854 | 2/1991 | European Pat. Off.. |
| 0 471 576 | 2/1992 | European Pat. Off.. |
| 0 506 363 | 9/1992 | European Pat. Off.. |
| WO 91/00856 | 1/1991 | WIPO. |
| WO 91/13872 | 9/1991 | WIPO. |

OTHER PUBLICATIONS

Foreman, et al., (Aug. 2, 1992) *Abstract Brit. Psychopharm Soc.,* Cambridge, UK.
Lucot, et al., (1988) *Pharm. Biochemistry & Behavior,* vol. 33, pp. 627–631.
Othmer, et al., (May 1987) *J. Clin. Psychiatry,* vol. 48, pp. 201–203.
Lucot, James B., (1992) *Mechanisms and Control of Emesis,* vol. 223, pp. 195–201.
Sanger, G. J., (1990) *Can. J. Physiol. Pharmacol.,* 68:314–324.
Lucot, James B., (1989) *Pharm. Biochemistry & Behavior,* vol. 37, pp. 283–287.
Allen, et al., (1974) Arzneim–Forsch, (*Drug Res.*) 24(6), pp. 917–922.
Preziosi, et al., (1992) *European Journal of Pharmacology,* 221, pp. 343–350.
Lucot, James B. (1988) *Pharmacology Biochemistry & Behavior,* vol. 32, pp. 207–210.
Lucot, et al., (1987) *J. Clin. Pharmacol.,* 27 pp. 817–818.
Lucot, et al., *Aviat. Space Envir. Med.,* 58, 989–991 (1987).
Taylor, Duncan, (1990) Ann. N.Y. Acad Sci., 600, pp. 545–557.
Flaugh, et al., (1988) *J. Med. Chem.,* 31, pp. 1746–1753.
Slaughter, et al., (1990) *Life Sci.,* 47(15), pp. 1331–1337.
Foreman, et al., (1990) *Sem. Urol.,* 8, (2), pp. 107–112.
Lucat, J & B., (1991) Soc. Neurosci. Abst. 17,92.

*Primary Examiner*—Joseph McKane
*Assistant Examiner*—Richard S. Myers, Jr.
*Attorney, Agent, or Firm*—Arleen Palmberg; Douglas J. Taylor

[57] ABSTRACT

The present invention provides methods of preventing emesis and treating sexual dysfunction in mammals utilizing certain tetrahydrobenz[cd]indoles. The invention further provides pharmaceutical formulations suitable for use in such methods.

9 Claims, No Drawings

METHOD OF PREVENTING EMESIS USING TETRAHYDROBENZ [CD]INDOLE-6-CARBONXAMIDES

This application is a continuation of application Ser. No. 08/075,198, filed on Jun. 10, 1993, abandoned.

BACKGROUND OF THE INVENTION

This invention provides a method of preventing emesis and in mammals as well as formulations suitable therefor.

Extensive research has been conducted for a number of years directed toward the development of compounds capable of preventing emesis and treating sexual dysfunction in mammals. For example, buspirone, 8-hydroxydipropylamino tetralin, yohimbine, scopolamine and various serotonin-3 antagonists have all been evaluated for prevention of emesis. However, to date, such compounds have proven unsatisfactory as anti-emetics for a variety of reasons including lack of user safety, insufficient efficacy, presence of undesirable side-effects and lack of broad spectrum anti-emetic activity. Similarly, bromocriptine, yohimbine, bupropion, naltrexone, methysergide, buspirone and gonadotropin releasing hormone have all been evaluated for treating sexual dysfunction. Again, to date, such compounds have proven unsatisfactory in treating sexual dysfunction for many of the same reasons described above.

It is an object of this invention to provide a new method for preventing emesis and treating sexual dysfunction in mammals, which method comprises administering a compound selected from among certain tetrahydrobenz[cd] indoles of the general formula

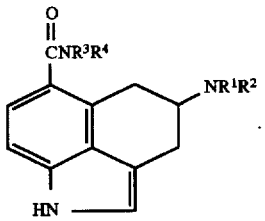

The tetrahydrobenz[cd]indoles utilized in the instantly claimed method are believed to provide a safe, broad spectrum, way of preventing emesis and treating sexual dysfunction with a minimum of side effects. As such, the instantly claimed method is believed to obviate many of the defects observed with compounds previously tested for treating sexual dysfunction and preventing emesis.

Since the present invention provides a new method for preventing emesis and treating sexual dysfunction in mammals, pharmaceutical formulations suitable for such new method will be required. Accordingly, a further object of this invention is to provide pharmaceutical formulations suitable for use in the instantly claimed method.

The objects of the present invention employ certain tetrahydrobenz[cd]indoles of the general formula

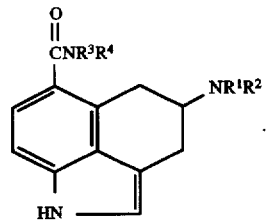

Such compounds are known in the art, as described below, and have been found to possess various utilities.

Flaugh, U.S. Pat. No. 4,576,959, discloses that the primary amino carboxamide compounds employed in the present invention (i.e., those compounds wherein $R^3$ and $R^4$ are both hydrogen) are central serotonin agonists. As such, the compounds are taught to be useful in treating depression, obesity, alcoholism, smoking and senile dementia. In fact, one of the compounds disclosed in the Flaugh patent; namely, (±)-4-dipropylamino-1,3,4,5-tetrahydrobenz[cd] indole-6-carboxamide, is presently undergoing clinical trials for use in treating depression in humans.

Leander, U.S. Pat. No. 4,745,126, discloses that the primary amino carboxamide compounds disclosed in the above-mentioned Flaugh patent are also useful for treating anxiety. In fact, one of the compounds disclosed in the Leander patent; namely, the 6-carboxamide compound described above, is also presently undergoing clinical trials for use in treating anxiety in humans.

Finally, European Patent Application 392,768 discloses that the substituted amino carboxamide compounds employed in the present invention (i.e., those compounds wherein either $R^3$ and/or $R^4$ are other than hydrogen) are useful in treating conditions requiring enhancement of serotonin function in the body. Such conditions are denoted as including depression, anxiety, alcoholism, obesity, smoking, sexual dysfunction and senile dementia.

The primary amino carboxamide compounds employed in the method of the present invention have not heretofore been disclosed as being useful for preventing emesis or treating sexual dysfunction in mammals. Further, the substituted amino carboxamide compounds employed in the method of the present invention have not heretofore been disclosed as being useful for preventing emesis. The known activities of such compounds, as described above, do not suggest the method of the present invention. Accordingly, an object of the present invention is to provide new pharmacological uses, and formations suitable therefore, for certain known tetrahydrobenz[cd]indoles.

Other objects, features and advantages of the present invention will become apparent from the subsequent description and the appended claims.

SUMMARY OF THE INVENTION

The present invention provides a method of preventing emesis and treating sexual dysfunction in mammals comprising administering to a mammal susceptible to or suffering from emesis or sexual dysfunction an effective amount of a compound of the formula I $$\text{(I)}$$

[Structure I: tetrahydronaphthalene with CNH$_2$(=O) group, NR$^1$R$^2$ substituent, and HN=CH group]

wherein:

R$^1$ is hydrogen, C$_1$–C$_4$ alkyl or allyl;

R$^2$ is hydrogen, C$_1$–C$_4$ alkyl or allyl; or a pharmaceutically acceptable acid addition salt thereof.

The present invention also provides a method of preventing emesis is mammals comprising administering to a mammal susceptible to or suffering from emesis an effective amount of a compound of the formula II $$\text{(II)}$$

[Structure II: tetrahydronaphthalene with CNR$^3$R$^4$(=O) group, NR$^1$R$^2$ substituent, and HN=CH group]

wherein:

R$^1$ is hydrogen, C$_1$–C$_4$ alkyl or allyl;

R$^2$ is hydrogen, C$_1$–C$_4$ alkyl or allyl;

R$^3$ and R$^4$ are each independently hydrogen, C$_1$–C$_4$ alkyl, C$_1$–C$_4$ alkyl substituted with a phenyl group, phenyl, or R$^3$ and R$^4$, taken together with the nitrogen atom to which they are attached, form a C$_3$–C$_5$ heterocyclic ring, with the proviso that only one of R$^3$ and R$^4$ can be hydrogen while the other of R$^3$ and R$^4$ must be other than hydrogen; or a pharmaceutically acceptable acid addition salt thereof.

Finally, since the present invention provides new methods for preventing emesis and treating sexual dysfunction in mammals, pharmaceutical formulations suitable for such methods will be required. Accordingly, the present invention also provides pharmaceutical formulations useful for preventing emesis and treating sexual dysfunction comprising a compound of formulae I or II, or a pharmaceutically acceptable acid addition salt thereof, in combination with one or more pharmaceutically acceptable carriers, diluents or excipients therefor.

DETAILED DESCRIPTION OF THE INVENTION

As used herein, the term "C$_1$–C$_4$ alkyl" represents a straight or branched chain alkyl group having from one to four carbon atoms. Typical C$_1$–C$_4$ alkyl groups include methyl, ethyl, n-propyl, isopropyl, n-butyl, sec-butyl and the like.

The term C$_3$–C$_5$ heterocyclic ring" includes pyrrolidine, piperidine, morpholine and the like.

While all of the compounds of formulae I and II are believed useful for the methods of treating emesis and sexual dysfunction presented herein, certain of the compounds of formulae I and II are preferred for such uses. Preferably R$^1$ and R$^2$ in formulae I and II are both C$_1$–C$_4$ alkyl (especially n-propyl) and R$^3$ and R$^4$ in formula II are either both methyl or R$^3$ is methyl while R$^4$ is hydrogen. Other preferred aspects of the present invention are noted hereinafter.

The pharmaceutically acceptable acid addition salts of the compounds of formulae I and II are also useful in the instantly disclosed methods of preventing emesis and treating sexual dysfunction. Accordingly, such salts are included within the scope of the methods of this invention.

The term "pharmaceutically acceptable acid addition salts", as used herein, refers to the acid addition salts of the compounds of formulae I and II which are substantially non-toxic to living organisms. Typical pharmaceutically acceptable acid addition salts include those salts prepared by reaction of the free base form of the compound of formulae I or II with a pharmaceutically acceptable mineral or organic acid. Pharmaceutically acceptable mineral or organic acids commonly employed to form such salts include inorganic acids such as hydrochloric, hydrobromic, hydroiodic, nitric, sulfuric and phosphoric acid, as well as organic acids such as paratoluenesulfonic, methane-sulfonic, hippuric, oxalic, parabromophenylsulfonic, carbonic, succinic, citric, benzoic, acetic, and related inorganic and organic acids. Such pharmaceutically acceptable salts thus include sulfate, pyrosulfate, bisulfate, sulfite, bisulfite, phosphate, monohydro-genphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate, hippurate, and like salts. A preferred pharmaceutically acceptable acid addition salt for use in the methods of the present invention is the hippurate salt. Such salt form, and processes for preparing same, is disclosed in European Patent Application 444,852, the teachings of which are hereby incorporated by reference.

The compounds employed in the methods of the present invention have an asymmetric center at the carbon atom at the 4-position of the tetrahydrobenz[cd]indole ring. As such, the compounds can exist as either the racemic mixture, or as individual stereoisomers. All such types of compounds are contemplated for use in the methods of the present invention.

The following list illustrates representative compounds suitable for use in the present invention.

(±)-4-(di-n-propylamino)-1,3,4,5-tetrahydrobenz[cd]indole-6-carboxamide oxalate (+)-4-amino, 1,3,4,5-tetrahydrobenz[cd]-indole-6-carboxamide maleate (−)-4-(methylamino)-1,3,4,5-tetrahydrobenz[cd]indole-6-carboxamide formate (−)-4-(diethylamino)-1,3,4,5-tetrahydrobenz[cd]indole-6-carboxamide (+)-4-(dimethylamino)-1,3,4,5-tetrahydrobenz[cd]indole-6-carboxamide oxalate (+)-4-(ethylamino)-1,3,4,5-tetrahydrobenz[cd]indole-6-carboxamide phosphate (±)-4-amino-1,3,4,5-tetrahydrobenz[cd]indole-6-carboxamide hydrochloride (±)-4-(n-propylamino)-1,3,4,5-tetrahydrobenz[cd]indole-6-carboxamide oxalate (±)-4-(methylamino)-1,3,4,5-tetrahydrobenz[cd]indole-6-carboxamide toluenesulfonate (−)-4-amino-1,3,4,5-tetrahydrobenz[cd]indole-6-carboxamide (+)-4-(methylethylamino)-1,3,4,5-tetrahydrobenz[cd]indole-6-carboxamide sulfate (−)-4-(diethylamino)-1,3,4,5-tetrahydrobenz[cd]indole-6-carboxamide (−)-4-amino-1,3,4,5-tetrahydrobenz[cd]indole-6-carboxamide propionate (+)-4-(dimethylamino)-1,3,4,5-tetrahydrobenz[cd]indole-6-carboxamide (±)-4-(diethylamino)-1,3,4,5-tetrahydrobenz[cd]indole-6-carboxamide hydroiodide (±)-4-amino-1,3,4,5-tetrahydrobenz[cd]indole-6-carboxamide (±)-4-(ethyl-n-propylamino)-1,3,4,5-tetrahydrobenz[cd]indole-6-carboxamide (±)-4-(di-n-propylamino)-1,3,4,5-tetrahydrobenz[cd]indole-6-carboxamide succinate (−)-4-(methyl-n-propylamino)-1,3,4,5-tetrahydrobenz[cd]indole-6-carboxamide (+)-4-(dimethylamino)-1,3,4,5-tetrahydrobenz[cd]indole-6-carboxamide sulfate (−)-4-amino-1,3,4,5-tetrahydrobenz[cd]indole-6-carboxamide maleate (+)-4-(diethylamino)-1,3,4,5-tetrahydrobenz[cd]indole-6-carboxamide (±)-4-(di-n-propylamino)-1,3,4,5-tetrahydrobenz[cd]indole-6-carboxamide hippurate (+)-4-(dimethylamino)-1,3,4,5-tetrahydrobenz[cd]indole-6-carboxamide (−)-4-(di-n-propylamino)-1,3,4,5-tetrahydrobenz[cd]indole-6-carboxamide acetate (±)-4-amino-1,3,4,5-tetrahydrobenz[cd]indole-6-carboxamide succinate (±)-4-(dimethylamino)-1,3,4,5-tetrahydrobenz[cd]indole-6-carboxamide citrate (±)-4-(di-n-propylamino)-1,3,4,5-tetrahydrobenz[cd]indole-6-carboxamide hydrobromide (−)-4-(ethyl-n-propylamino)-1,3,4,5-tetrahydrobenz[cd]indole-6-carboxamide benzoate (+)-4-(methyl-n-propylamino)-1,3,4,5-tetrahydrobenz[cd]indole-6-carboxamide phthalate (+)-4-(methylethylamino)-1,3,4,5-tetrahydrobenz[cd]indole-6-carboxamide (+)-4-(methylallylamino)-1,3,4,5-tetrahydrobenz[cd]indole-6-carboxamide mesylate (−)-4-(di-n-propylamino)-1,3,4,5-tetrahydrobenz[cd]indole-6-carboxamide maleate (+)-4-(diallylamino)-1,3,4,5-tetrahydrobenz[cd]indole-6-carboxamide succinate (−)-4-amino-1,3,4,5-tetrahydrobenz[cd]indole-6-carboxamide fumarate (+)-4-(di-n-propylamino)-1,3,4,5-tetrahydrobenz[cd]indole-6-carboxamide (+)-4-(diethylamino)-1,3,4,5-tetrahydrobenz[cd]indole-6-carboxamide acetate (±)-4-(ethylamino)-1,3,4,5-tetrahydrobenz[cd]indole-6-carboxamide (−)-4-amino-1,3,4,5-tetrahydrobenz[cd]indole-6-carboxamide (+)-4-(methylamino)-1,3,4,5-tetrahydrobenz[cd]indole-6-carboxamide (+)-4-(n-propylamino)-1,3,4,5-tetrahydrobenz[cd]indole-6-carboxamide hydrobromide (+)-4-(di-n-propylamino)-1,3,4,5-tetrahydrobenz[cd]indole-6-carboxamide (±)-4-(methylethylamino)-1,3,4,5-tetrahydrobenz[cd]indole-6-carboxamide hydroiodide (+)-4-(allylamino)-1,3,4,5-tetrahydrobenz[cd]indole-6-carboxamide malonate (±)-4-(diethylamino)-1,3,4,5-tetrahydrobenz[cd]indole-6-carboxamide (±)-N,N-dimethyl-4-(di-n-propylamino)-1,3,4,5-tetrahydrobenz[cd]indole-6-carboxamide (±)-N-methyl-4-(di-n-propylamino)-1,3,4,5-tetrahydrobenz[cd]indole-6-carboxamide (±)-N,N-diethyl-4-(di-n-propylamino)-1,3,4,5-tetrahydrobenz[cd]indole-6-carboxamide As noted hereinbefore, the compounds employed in the methods of the present invention are known. For example, methods of preparing the compounds of formula I are taught in U.S. Pat. Nos. 4,576,959 and 4,745,126, while methods of preparing the compounds of formula II are taught in U.S. Pat. No. 5,204,340. A preferred method for preparing the compounds of formulae I and II, and, in particular, the stereoisomers of such compounds, is taught in U.S. patent application Ser. No. 07/799,924 (issue fee paid) and its European patent application cognate EP 444,851. The teachings of all such patents and patent applications are hereby incorporated by reference.

The present invention provides methods of preventing emesis and treating sexual dysfunction in mammals. Such activities were demonstrated in the following test systems.

Emesis

Adult female cats of mixed strains were obtained and housed such that they had free access to food and water except during the time of testing. Cats were selected for these studies based upon a minimum of 2 emetic episodes in 5 tests in response to a 30 minute rotation (0.28 Hz, 17 rpm) on a motion device such as that described in Crampton, et al., *Aviat. Space Environ. Med.,* 56, pp. 462–465 (1985). Single emetic response tests were conducted at intervals of at least two weeks to prevent habituation to the motion stimulus. Baseline responses (occurrence of retching and vomiting) to motion following saline pretreatment were determined before and after the evaluation of a test compound. Subjects received subcutaneous injections of a test compound in sterile saline to an injection volume of 0.1 mg/kg or vehicle 30 minutes before motion testing. The order of the testing was saline, 0.02, 0.005, 0.01, 0.0075, 0.0025 mg/kg test compound and saline. The binomial data for retch/vomits were analyzed using Cochrane's Q test and McNewmar's test for repeated measures. The results of such testing are reported in Table I below.

TABLE I

Suppression of Motion Sickness in Cats

| Treatment* | Dose of Test Compound (mg/kg) | # vomiting / # tested | Change in Test Subject's behavior observed |
|---|---|---|---|
| Saline | — | 7/13 | No |
| Test Compound | 0.0025 | 6/13 | No |
| Test Compound | 0.005 | 5/13 | No |
| Test Compound | 0.0075 | 1/13+ | No |
| Test Compound | 0.010 | 0/11+ | No |
| Test Compound | 0.020 | 0/11+ | No |
| Saline | — | 13/13 | No |

*Test compound employed was (−)-4-dipropylamino-1,3,4,5-tetrahydrobenz[cd]indole-6-carboxamide
+Significant difference (p < .05) from control group A group of 16 male White Carneaux pigeons, weighing approximately 460 to 650 g (85–90% of their free-feeding body weights) were also tested. Animals were given free access to water and oyster shell grit except during the test sessions and were fed approximately 20 g of grain-based feed (Purina Pigeon Checkers) once per day. The colony room was illuminated from 6 a.m. to 6 p.m. daily. All testing was conducted during the illuminated phase.

The pigeons were first fed 20 grams of Purina Pigeon Checkers in their home cages. Five minutes later, the birds were weighed and injected intravenously with either 10 or 13 mg/kg of cisplatin (cis-platinum II diammine dichloride; Signma Chemical Co., St. Louis, Mo.) and then placed in a plexiglas observation cage. After 45 minutes, either vehicle, 0.08, or 0.32 mg/kg of test compound were administered by intramuscular injection. The test compound was dissolved in distilled water with the aid of a few drops of lactic acid. The animals were then observed for the next 4.5 hours for the number of both retches and vomits. A vomit was considered to be the active expulsion of fluid or solid matter, whereas retches were considered to be vomiting movements without expulsion of matter. Each pigeon was used only once, and they were terminated immediately after the 4.5 hour observation period. The results of such testing are shown in the Table II below.

TABLE II

Suppression of Cisplatin Induced Emesis in Pigeons

| Treatment* | Dose of Cisplatin (mg/kg) | Dose of Test Compound (mg/kg) | # of Pigeons | # of Retches | # of Vomits |
|---|---|---|---|---|---|
| Vehicle | 10 | — | 4 | 2.0 ± 0.73 | 4.8 ± 1.59 |
| Test Compound | 10 | 0.08 | 4 | 3.25 ± 1.65 | 3.0 ± 1.22 |
| Test Compound | 10 | 0.32 | 4 | 0 | 0 |
| Vehicle | 13 | — | 2 | 1.5 | 6 |
| Test Compound | 13 | 0.32 | 2 | 0 | 0 |

*Test compound employed was (−)-4-dipropylamino-1,3,4,5-tetrahydrobenz[cd]indole-6-carboxamide.

Another group of 20 male White Carneaux pigeons, weighing approximately 460 to 650 g (85–90% of their free-feeding body weights) were also tested using ditolylguanidine (DTG in place of cisplatin to induce emesis. Animals were given free access to water and oyster shell grit except during the test sessions and were fed approximately 20 g of grain-based feed (Purina Pigeon Checkers) once per day. The colony room was illuminated from 6 a.m. to 6 p.m. daily. All testing was conducted during the illuminated phase.

The pigeons were first fed 20 grams of Purina Pigeon Checkers in their home cages. Five minutes later, the birds were weighed, injected with various doses of test compound and returned to their home cages. The test compound was dissolved in distilled water with the aid of a few drops of lactic acid. All injections were given into the breast muscle in a volume of 1 ml/kg. After 15 minutes, a 5.6 mg/kg dose of DTG was administered and the pigeons were placed into Plexiglas observation chambers. One hour later, the birds were removed from the observation chambers and returned to their home cages and the floor of the observation cage was examined for the presence of expelled food. The dependent variable in the instant study was the percent of birds at each dose that exhibited evidence of expelled food. The results of such study are presented in Table III below.

TABLE III

Suppression of Ditolylguanidine Induced Emesis in Pigeons

| Dose of Test Compound* (mg/kg) | Percent of Pigeons Vomiting |
|---|---|
| 0.01 | 100 |
| 0.02 | 75 |
| 0.04 | 50 |
| 0.08 | 25 |
| 0.16 | 0 |

*Test compound employed was (−)-4-dipropylamino-1,3,4,5-tetrahydrobenz[cd]indole-6-carboxamide The data in Tables I, II and III establish that compounds of formulae I and II can be used to prevent emesis. The term "emesis", as used for purposes of the present invention, means vomiting (the actual expulsion of stomach contents), retching (vomiting movements without expulsion of matter) and the concomitant nausea associated with such conditions. Accordingly, the compounds of formulae I and II can be used to suppress emetic responses to provocative motion (motion sickness) and various chemical stimuli such as oncolytic agents (e.g., cisplatin) or other psychoactive agents (e.g., xylazine, analgesics, anesthetics and dopaminergic agents) and the like.

Sexual Dysfunction

Male Sprague-Dawley rats and ovariectomized, Long-Evans rats purchased from Charles River Laboratories (Portage, Mich.) were used in this study. All of the rats were housed in a temperature controlled room in which the lights were off from 10:00 to 20:00. The ovariectomized rats used as sexual partners for the test males were made sexually receptive by administering 400 μg of estrone in propylene glycol subcutaneously 48 hours prior to testing and 2.5 mg of progesterone in propylene glycol subcutaneously 4 hours prior to testing. The male rats were individually housed beginning 4 weeks prior to testing and were tested at 2 week intervals beginning at 6 months of age and ending at 12 months of age using the procedure previously published in Foreman, et al., *J. Neural. Trans.*, 68, pp. 153–170 (1987). Mating tests were conducted between 12:00 and 17:00 during the dark phase of the lighting cycle. Each behavioral test was initiated with the introduction of a receptive female rat into the arena and was terminated either 30 minutes later or immediately following the first postejaculatory mount.

Prior to treatment with a drug solution, each male rate was required to have at least two consecutive vehicle tests with similar sexual performance. Following each drug testing, additional vehicle tests were performed. In an effort to eliminate behavioral responses with drug treatment that may be due to spontaneous changes in baseline mating performance, a criterion of reversibility of behavioral response with subsequent vehicle treatment was used. Thus, a valid behavioral response to a drug treatment was arbitrarily set as a response that either did not change from the prior control response or was reversed in the subsequent control test with vehicle. Statistical comparisons between the sexual responses to vehicle and drug treatments for each animal were made using the Wilcoxon paired-sample test. The results of such testing are reported in Table IV below.

In Table IV, Column 1, discloses the dose of test compound administered to each test subject. Columns 2 and 3 disclose the percent change from control of ejaculatory latency and total number of mounts required for ejaculation, respectively, for each dose tested. Finally, Columns 4 and 5 disclose the percent change from control of copulatory efficiency and copulatory rate, respectively, for each dose tested.

ceutical compositions which are prepared by techniques well known in the pharmaceutical sciences.

The methods of the present invention encompass prevention of emesis and treatment of sexual dysfunction in a prophylactic manner (i.e., using the compounds of formulae I and II to prevent emesis or treat sexual dysfunction in a mammal susceptible to such conditions before the conditions actually occur or re-occur). Such prophylactic method of administration may be especially appropriate in cases where the patient is susceptible to motion sickness and is about to go on a boat, car or plane trip which, normally, would result in the patient's suffering a motion sickness attack; the patient is about to undergo treatment with various chemical stimuli (cancer chemo and radiation therapy, analgesic and anesthetic agents, etc.) known to cause emesis; the patient is about to undergo or is undergoing treatment with an anxiolytic, such as a benzodiazepine, or an antidepressant, such as a 5-HT reuptake inhibitor or a tricyclic antidepressant, which is known to cause sexual disorders; the patient has experienced sexual dysfunction in the past, is about to engage in sexual intercourse and wishes to prevent a reoccurrence of the dysfunction; or the patient wishes to increase his or her sexual drive.

TABLE IV

TREATMENT OF SEXUAL DYSFUNCTION IN RATS

| Dose of Test* Compound Administered (μg/kg, s.c.) | Percent Change From Control in | | Percent Change From Control in | |
|---|---|---|---|---|
| | Ejaculatory Latency | # of Mounts Required for Ejaculation | Copulatory** Efficiency | Copulatory Rate |
| 0 (vehicle control) | +0.4 ± 2.7 | +20.5 ± 8.4 | +7.0 ± 6.2 | +23.4 ± 9.1 |
| 1.0 | −20.6 ± 8.3⁺ | −7.2 ± 10.3 | +7.4 ± 14.6 | +11.8 ± 9.4 |
| 10 | −27.9 ± 3.6⁺ | −20.9 ± 7.8⁺ | +21.9 ± 15.8 | +9.9 ± 9.0 |
| 100 | −55.7 ± 4.8⁺ | −34.1 ± 6.5⁺ | +36.4 ± 11.4⁺ | +62.2 ± 17.7 |

*Test compound employed was (−)-4-dipropylamino-1,3,4,5-tetrahydrobenz[cd]indole-6-carboxamide
**Defined as # intromissions/total # of mounts
⁺Significant difference from control The data in Table IV establishes that compounds of formula I can be used to treat sexual dysfunction. The term "sexual dysfunction", as used herein, means any disorder related to the erectile response in male mammals and the sexual drive and sexual (both arousal and orgamsmic) reflexes in male or female mammals. Accordingly, the compounds of formula I can be used to treat erectile dysfunction, retarded ejaculation and an orgasm. The compounds can, further, also be used to increase sexual desire in mammals of both sexes.

As discussed above, the compounds of formulae I and II are physiologically active thereby lending themselves to the valuable therapeutic methods claimed herein. These methods comprise administering to a mammal (preferably a human) needing prevention of emesis or treatment of sexual dysfunction an effective amount of one or more compounds of formulae I (emesis and sexual dysfunction) or II (emesis alone) sufficient to achieve the therapeutic or prophylactic intervention desired. The compounds can be administered by a variety of routes including the oral, rectal, transdermal, subcutaneous, intravenous, intramuscular or intranasal routes. The oral and transdermal routes of administration are preferred. No matter what route of administration is chosen, such administration is accomplished by means of pharma- As mentioned above, the methods of the present invention utilize pharmaceutical compositions. In making these compositions, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic or prophylactic effect, in association with one or more suitable pharmaceutical diluents, excipients or carriers.

The compounds employed in the methods of the present invention are effective over a wide dosage range for preventing emesis and treating sexual dysfunction. Thus, as used herein, the term "effective amount" refers to a dosage range of from about 0.5 to about 500 mg/kg of body weight per day. In the treatment of adult humans, the range of about 1 to about 100 mg/kg, in single or divided doses, is preferred. However, it will be understood that the amount of compound actually administered will be determined by a physician, in light of the relevant circumstances including the condition to be treated, the choice of compound to be administered, whether prophylactic or therapeutic effect is desired, the chosen route of administration, the age, weight, and response of the individual patient, and the severity of the patient's symptoms, and, therefore, the above dosage ranges are not intended to limit the scope of the invention in any way.

The following formulation examples may employ as active ingredients any of the compounds of formulae I or II. The examples are illustrative only and are not intended to limit the scope of the invention in any way.

EXAMPLE 1

Hard gelatin capsules suitable for preventing emesis are prepared using the following ingredients:

|  | Quantity (mg/capsule) |
|---|---|
| (±)-4-dipropylamino-1,3,4,5-tetrahydrobenz[cd]indole-6-carboxamide hippurate | 250 |
| Starch dried | 200 |
| Magnesium stearate | 10 |

The above ingredients are mixed and filled into hard gelatin capsules in 460 mg quantities.

EXAMPLE 2

A tablet suitable for preventing emesis is prepared using the ingredients below:

|  | Quantity (mg/tablet) |
|---|---|
| (±)-N-methyl-4-dipropylamino-1,3,4,5-tetrahydrobenz[cd]indole-6-carboxamide hydrochloride | 250 |
| Cellulose, microcrystalline | 400 |
| Silicon dioxide | 10 |
| Stearic acid | 5 |

The components are blended and compressed to form tablets each weighing 665 mg.

EXAMPLE 3

An aerosol solution suitable for treating sexual dysfunction is prepared containing the following components:

|  | Weight |
|---|---|
| (+)-4-diethylamino-1,3,4,5-tetrahydrobenz[cd]indole-6-carboxamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. Valve units are then fitted to the container.

EXAMPLE 4

Tablets suitable for treating sexual dysfunction, each containing 60 mg of active ingredient are made up as follows:

|  |  |
|---|---|
| (+)-4-diethylamino-1,3,4,5-tetrahydrobenz[cd]indole-6-carboxamide | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 5

Capsules suitable for preventing emesis, each containing 80 mg of medicament, are made as follows:

|  |  |
|---|---|
| (±)-N-methyl-4-diethylamino-1,3,4,5-tetrahydrobenz[cd]indole-6-carboxamide hippurate | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 6

Suppositories suitable for treating sexual dysfunction, each containing 225 mg of active ingredient, are made as follows:

| | |
|---|---|
| (±)-4-diallylamino-1,3,4,5-tetrahydrobenz[cd]indole-6-carboxamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions suitable for preventing emesis, each containing 50 mg of medicament per 5 ml dose, are made as follows:

| | |
|---|---|
| (−)-N,N-diethyl-4-dipropyl-amino-1,3,4,5-tetrahydrobenz[cd]-indole-6-carboxamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 8

Capsules suitable for use in treating sexual dysfunction, each containing 150 mg of medicament, are made as follows:

| | |
|---|---|
| (−)-4-dipropylamino-1,3,4,5-tetrahydrobenz[cd]indole-6-carboxamide hippurate | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A method of preventing emesis in mammals comprising administering to a mammal susceptible to or suffering from emesis an effective amount of a compound of the formula

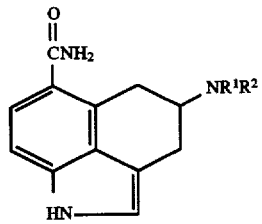

wherein:

$R^1$ is hydrogen, $C_1$–$C_4$ alkyl or allyl;

$R^2$ is hydrogen, $C_1$–$C_4$ alkyl or allyl; or a pharmaceutically acceptable acid addition salt thereof.

2. A method of claim 1 wherein the mammal is a human.

3. A method of claim 2 wherein in the compound employed $R^1$ and $R^2$ are each independently $C_1$–$C_4$ alkyl.

4. A method of claim 3 wherein in the compound employed is (±)-4-dipropylamino-1,3,4,5-tetrahydrobenz[cd]indole-6-carboxamide or a pharmaceutically acceptable acid addition salt thereof.

5. A method of claim 4 wherein the acid addition salt is the hippurate salt.

6. A method of claim 3 wherein the compound employed is (−)-4-dipropylamino-1,3,4,5-tetrahydrobenz[cd]indole-6-carboxamide or a pharmaceutically acceptable acid addition salt thereof.

7. A method of claim 6 wherein the acid addition salt is the hippurate salt.

8. A method of claim 3 wherein the compound employed is (+)-4-dipropylamino-1,3,4,5-tetrahydrobenz [cd]indole-6-carboxamide or a pharmaceutically acceptable acid addition salt thereof.

9. A method of claim 8 wherein the acid addition salt is the hippurate salt.

* * * * *